United States Patent
Novelo Ascencio

(10) Patent No.: US 11,298,438 B1
(45) Date of Patent: Apr. 12, 2022

(54) INTELLIGENT DEVICE FOR HAND HYGIENE AND MOBILE DEVICE DISINFECTION

(71) Applicant: Aldo Ivan Novelo Ascencio, Zapopan (MX)

(72) Inventor: Aldo Ivan Novelo Ascencio, Zapopan (MX)

(*) Notice: Subject to any disclaimer, the term of this patent is extended or adjusted under 35 U.S.C. 154(b) by 0 days.

(21) Appl. No.: 17/246,554

(22) Filed: Apr. 30, 2021

(51) Int. Cl.
| | |
|---|---|
| *A61L 2/24* | (2006.01) |
| *A61L 2/00* | (2006.01) |
| *G07C 9/00* | (2020.01) |
| *G08B 21/24* | (2006.01) |

(52) U.S. Cl.
CPC ............ *A61L 2/24* (2013.01); *A61L 2/0088* (2013.01); *G07C 9/00896* (2013.01); *G08B 21/245* (2013.01); *A61L 2202/14* (2013.01); *A61L 2202/15* (2013.01)

(58) Field of Classification Search
CPC ...... A61L 2/24; A61L 2/0088; A61L 2202/14; A61L 2202/15
See application file for complete search history.

(56) References Cited

U.S. PATENT DOCUMENTS

| | | | | |
|---|---|---|---|---|
| 5,823,390 A | * | 10/1998 | Muderlak | A47K 5/1217 222/38 |
| 2009/0224924 A1 | * | 9/2009 | Thorp | G08B 21/245 340/573.1 |
| 2018/0280554 A1 | * | 10/2018 | Khajavi | A61L 2/24 |
| 2018/0357385 A1 | * | 12/2018 | LaPorte | A61L 2/10 |

* cited by examiner

*Primary Examiner* — Kevin Joyner
(74) *Attorney, Agent, or Firm* — Cognition IP, P.C.; Edward Steakley

(57) ABSTRACT

Systems and methods provide for intelligent hand hygiene and mobile device disinfection at a hand hygiene device. In one embodiment, the system detects, via a number of sensors, that a user is in proximity to the hand hygiene device, then provides instructions for the device to open a door to a compartment within the device. The system detects that a mobile device has been placed within the compartment, closes the door to the compartment, and performs disinfection of the mobile device within the compartment. Concurrently to performing disinfection of the mobile device, the system detects that at least one hand of the user has been placed under a dispensing component of the hand hygiene device, and then instructs the dispensing component to dispense hand sanitizer without the user coming into physical contact with the hand hygiene device. Upon completion of the disinfecting of the mobile device, the system opens the door to the compartment to release the mobile device to the user.

18 Claims, 15 Drawing Sheets

INTELLIGENT DEVICE FOR HAND HYGIENE AND MOBILE DEVICE DISINFECTION

CROSS-REFERENCE TO RELATED APPLICATIONS

This application claims priority to Mexican Patent Application No. MX/u/2020/000639, filed on Dec. 17, 2020, which is hereby incorporated by reference in its entirety.

FIELD OF INVENTION

The present invention relates generally to hygiene and sanitation, and more particularly, to systems and methods providing for intelligent hand hygiene and mobile device disinfection.

BACKGROUND

Hand hygiene has been widely studied and documented to be the best and most effective measure to prevent the acquisition and transmission of infectious diseases in all environments, as it eliminates pathogens that might be present on the hands, which in turn are in frequent contact with the eyes, nose, and mouth, therefore giving such pathogens a route into our bodies for infection. Hand hygiene becomes especially crucial in clinical and healthcare settings, where patient's health is of the upmost importance.

Also relevant to the prevention of the spread of diseases is the ubiquity of mobile devices which are carried around on the person and are frequently interacted with. Mobile devices tend to be intensively used throughout the day, and have become essential items in people's lives all over the world. Unfortunately, studies have shown that mobile devices such as smartphones can potentially act as infection sources, as they harbor different pathogens collected from surfaces or from the user's hands. Mobile devices can contain up to ten times more pathogens than a public restroom, and thus contribute to a significant risk of people contracting and spreading diseases.

Current guidelines for cleaning mobile phones consist of the use of wet wipes or alcohol wipes, chemicals, and microfiber cloths. Such manual methods of cleaning devices are impractical at a higher scale and need for disinfection of mobile devices at increased volumes. They are also impractical methods, as such materials are often not available nearby, nor are they carried by users of mobile devices on a regular basis. In addition, even if a mobile phone is disinfected manually, users rarely sanitize their hands at the same time, making it likely that recently disinfected mobile devices will become potential vectors for spreading disease once again shortly afterwards.

Thus, there is a need in the field of hygiene compliance and sanitation to create a new and useful system and method for intelligent hand hygiene and mobile device disinfection. The source of the problem, as discovered by the inventors, is a lack of a system which provides both mobile device disinfection and hand hygiene concurrently, and at higher volumes of disinfection, to eliminate pathogens present on a user's mobile device and hands in an automated and intelligent manner.

SUMMARY

The invention overcomes the existing problems by providing intelligent hand hygiene and mobile device disinfection at a hand hygiene device within an environment (e.g., a hospital or other clinical setting, or any other suitable environment). The hand hygiene device facilitates improvement of hand hygiene through one or more methods, such as audio and/or visual reinforcements within clinical environments.

The hand hygiene device includes a dispensing component configured to dispense hand sanitizer into a user's hands. The hand hygiene device operates automatically, without the user coming into physical contact with the device or its components in any way. This provides for a "hands free", "touch free" solution for hand sanitization. One or more sensors within the device are configured to detect a user's hand(s) once they are placed under the dispensing component. In some embodiments, the dispensing component can accept different formulas of sanitizing solutions and different types and sizes of containers for such solutions. In some embodiments, the device includes a container built to fit within the device which can be used for filling and refilling hand sanitizer. The dispensing component can allow a designated individual to effortlessly swap out a hand sanitizer container and swap in another of a different type or size as needed.

In order to reduce cross-contamination due to dirty hands, the unit is further equipped with a compartment for disinfection of mobile devices. In some embodiments, the disinfection occurs through the use of germicidal UV-C light. The device is configured to detect that a user has placed a mobile device within the compartment, close a door of the compartment, and perform disinfection of the mobile device. While the disinfection is in process, the user may place their hands under the dispensing component, receive dispensed hand sanitizer, and clean their hands following best hygiene practices. The compartment can then open once the disinfection is complete, allowing the user to remove the mobile device and continue on their way.

In some embodiments, the device thus may provide both hand hygiene and mobile device disinfection in the same moment, within a simplified, easy-to-operate unit which performs its actions within a matter of seconds, taking no more time than conventional hand cleaning.

In some embodiments, the usage data collected by the device is made accessible to designated users, who may access the data remotely through, e.g., a computer, a smartphone, or other client device. The system may also allow such designated users to control or modify content provided by the screen and/or speaker to provide feedback or reinforcement to users with respect to hand hygiene.

In one embodiment, the system detects, via a number of sensors, that a user is in proximity to the hand hygiene device, then provides instructions for the device to open a door to a compartment within the device. The system detects that a mobile device has been placed within the compartment, closes the door to the compartment, and performs disinfection of the mobile device within the compartment. Concurrently to performing disinfection of the mobile device, the system detects that at least one hand of the user has been placed under a dispensing component of the hand hygiene device, and then instructs the dispensing component to dispense hand sanitizer without the user coming into physical contact with the hand hygiene device. Upon completion of the disinfecting of the mobile device, the system opens the door to the compartment to release the mobile device to the user.

In some embodiments, the system provides, via a screen and/or one or more speakers on the hand hygiene device, audiovisual content during the disinfection of the mobile device, the dispensing of the hand sanitizer, or both. In some embodiments, the system can receive one or more requests from a client device to remotely modify the audiovisual content, and then modify the audiovisual content in response to those requests. In some embodiments, the audiovisual content includes positive reinforcement messages encouraging users to improve hand hygiene and mobile device disinfection compliance.

Further areas of applicability of the present disclosure will become apparent from the detailed description, the claims and the drawings. The detailed description and specific examples are intended for illustration only and are not intended to limit the scope of the disclosure.

BRIEF DESCRIPTION OF THE DRAWINGS

The present invention relates generally to digital communication, and more particularly, to systems and methods providing for containment of sensitive data within a communication or messaging platform.

The present disclosure will become better understood from the detailed description and the drawings, wherein.

DETAILED DESCRIPTION

Figure 1:
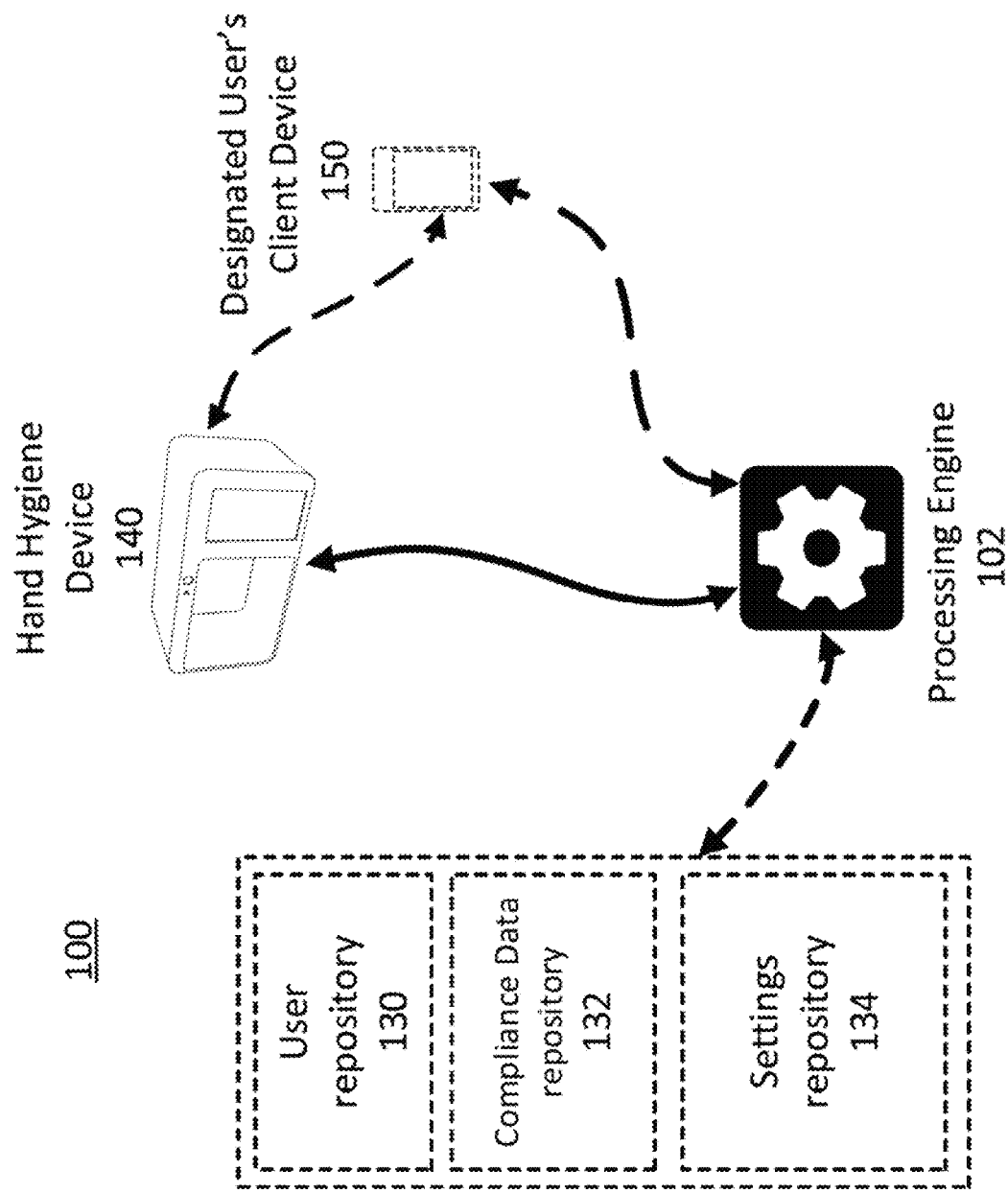
FIG. 1 is a diagram illustrating an exemplary environment in which some embodiments may operate.

In this specification, reference is made in detail to specific embodiments of the invention. Some of the embodiments or their aspects are illustrated in the drawings.

For clarity in explanation, the invention has been described with reference to specific embodiments, however it should be understood that the invention is not limited to the described embodiments. On the contrary, the invention covers alternatives, modifications, and equivalents as may be included within its scope as defined by any patent claims. The following embodiments of the invention are set forth without any loss of generality to, and without imposing limitations on, the claimed invention. In the following description, specific details are set forth in order to provide a thorough understanding of the present invention. The present invention may be practiced without some or all of these specific details. In addition, well known features may not have been described in detail to avoid unnecessarily obscuring the invention.

In addition, it should be understood that steps of the exemplary methods set forth in this exemplary patent can be performed in different orders than the order presented in this specification. Furthermore, some steps of the exemplary methods may be performed in parallel rather than being performed sequentially. Also, the steps of the exemplary methods may be performed in a network environment in which some steps are performed by different computers in the networked environment.

Some embodiments are implemented by a computer system. A computer system may include a processor, a memory, and a non-transitory computer-readable medium. The memory and non-transitory medium may store instructions for performing methods and steps described herein.

Intelligent Hand Hygiene Compliance Device

I. Exemplary Environments

FIG. 1A is a diagram illustrating an exemplary environment in which some embodiments may operate. In the exemplary environment 100, a designated user's client device 150 is optionally connected to a processing engine 102 and a hand hygiene device 140. The processing engine 102 is connected to the hand hygiene device 140, and optionally connected to one or more repositories and/or databases, including a user repository 130, compliance data repository 132, and/or a settings repository 134. One or more of the databases may be combined or split into multiple databases. The designated user's client device 150 and hand hygiene device in this environment may either or both be a computer or contain elements of a computer, and the processing engine 102 may be an application or software hosted on a computer or multiple computers which are communicatively coupled via remote server or locally.

The exemplary environment 100 is illustrated with only one designated user's client device, one processing engine, and one hand hygiene device, though in practice there may be more or fewer designated users' client devices, processing engines, and/or hand hygiene devices. In some embodiments, the processing engine and/or hand hygiene device may be part of the same computer or device.

Figure 2:
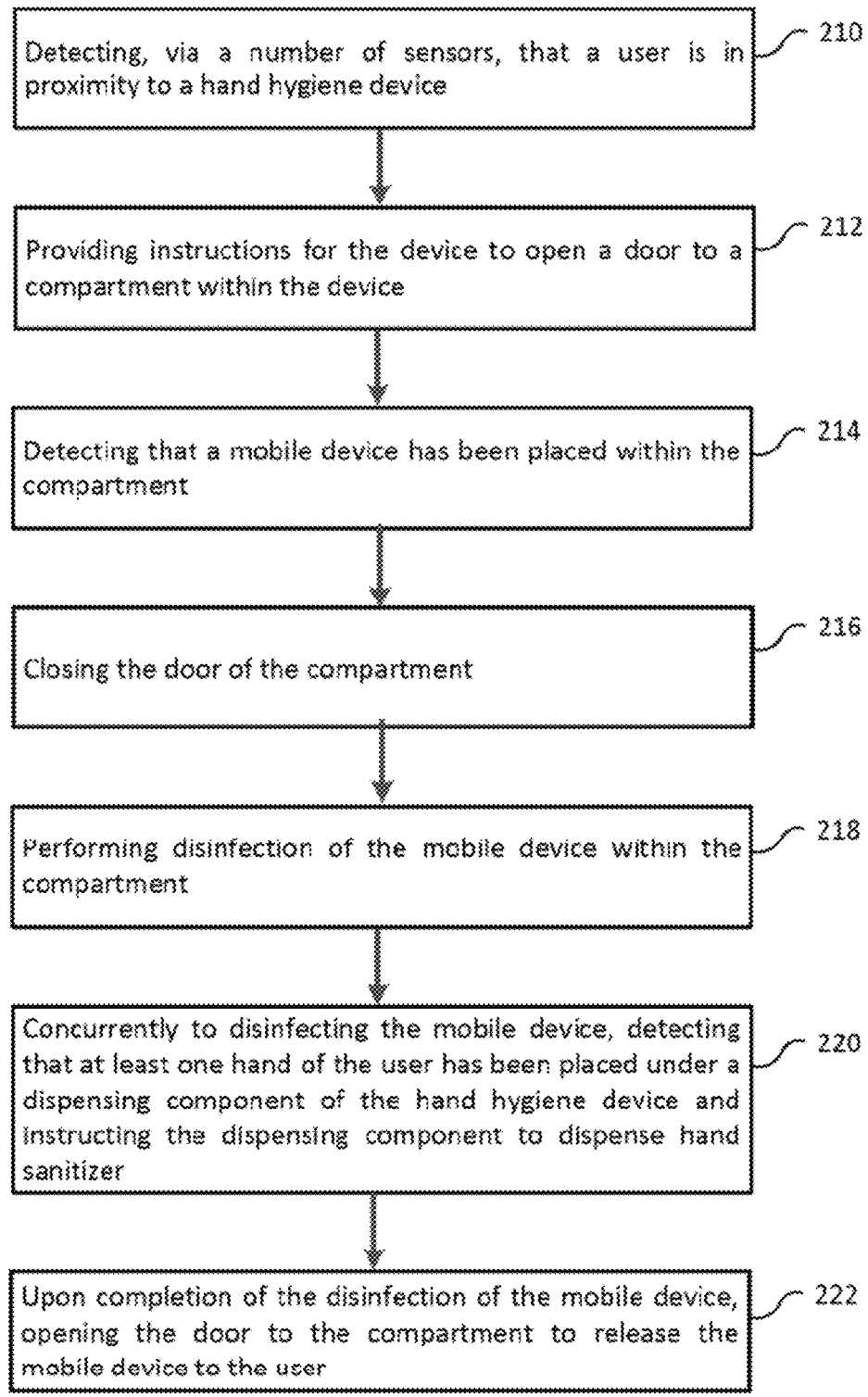
FIG. 2 is a flow chart illustrating an exemplary method that may be performed in some embodiments.
Figure 3:
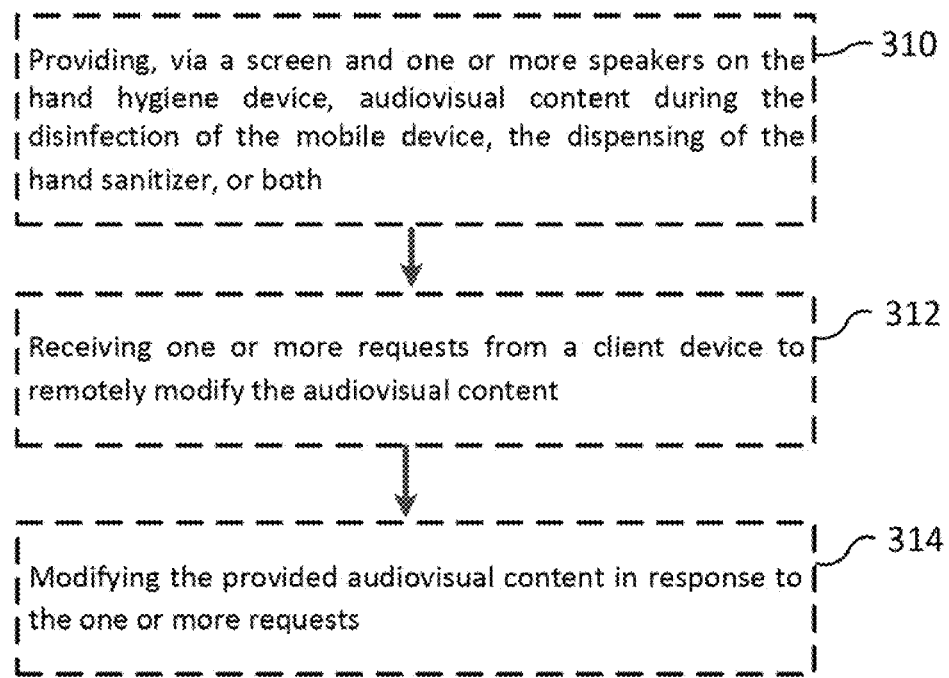
FIG. 3 is a flow chart illustrating an optional exemplary method that may be performed in some embodiments.
Figure 5:
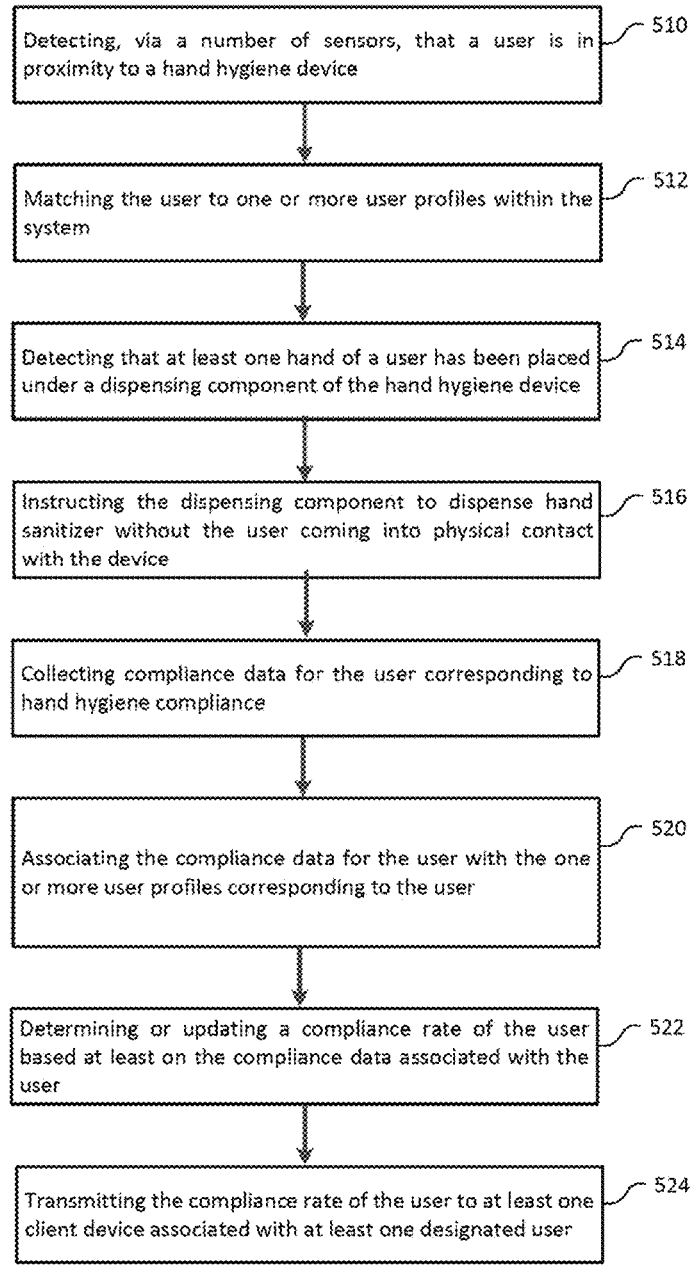
FIG. 5 is a flow chart illustrating an exemplary method that may be performed in some embodiments.

In an embodiment, the hand hygiene device 140 is a device which, in conjunction with the processing engine 102, may perform the exemplary methods of FIG. 2, FIG. 3, FIG. 5, or another method herein and, as a result, provide the ability for users to comply with hand hygiene standards in an environment. The hand hygiene device functions to provide at least a hand hygiene and sanitization process in such a way that it can be operated by users in a hands-free and touch-free fashion, in order to mitigate the spread of bacteria which can occur when several users touch the same surfaces in succession. The hand hygiene device includes an enclosure with one or more built-in compartments. One compartment is a sanitizer dispensing compartment, which functions to dispense hand sanitizer into a user's hands when they are placed inside of the sanitizer dispensing compartment. A hand sanitizer container is situated inside of the enclosure, and may be hidden from the view of the user.

In some embodiments, an additional built-in compartment is included for mobile device disinfection. Mobile devices to be disinfected may include, e.g., smartphones, tablets, smartwatches, or any other mobile device. In some embodiments, the hand hygiene device is configured to disinfect a mobile device upon the user inserting the mobile device into the compartment for mobile device disinfection. In some embodiments, the disinfection is performed via the optical radiation of UV-C light, also known as germicidal light. The UV-C light is irradiated to the mobile devices safely within a compartment. In some embodiments, one or more automatic doors may be present for the compartment. The system is capable of automatically closing a compartment shut without requiring any input from the user, in order to, e.g., stop the exposure of UV-C irradiation to the user.

In some embodiments, the hand hygiene device may be mounted to a wall or to horizontal surfaces, while in other cases the hand hygiene device may be a free-standing unit within an open area and mounted within a stand or other supporting component within an environment.

The hand hygiene device also includes a number of sensors. The sensors may be used to, e.g., detect the presence of a hand inside of the dispensing component, or detect the placement of a mobile device into a device disinfection component. In some embodiments, the sensors may be used to identify a user (e.g., a user's face).

In some embodiments, the hand hygiene device further includes a screen and/or speakers, which are used to display audio and/or visual information. This information may include marketing or advertising content, information on a user's hand hygiene compliance, information on the aggregated hand hygiene compliance of all users who made use of the device, information on the aggregated hand hygiene compliance of a group of users or a designated area within the environment, or any other suitable information. In some embodiments, the information presented is modifiable remotely by designated users, via such methods as, e.g., an application on a mobile device associated with the designated user. The hand hygiene device and its various components and possibilities will be discussed in further detail below.

In an embodiment, the processing engine 102 may perform the exemplary methods of FIG. 2, FIG. 3, FIG. 5, or other method herein and, as a result, instruct the hand hygiene device and its various components to perform certain actions depending on the needs of designated users as well as non-designated users. In some embodiments, this may be accomplished via communication with the designated user's client device and/or other device(s) over a network between the device(s) and an application server or some other network server. In some embodiments, the processing engine 102 is an application, browser extension, or other piece of software hosted on a computer or similar device, or is itself a computer or similar device configured to host an application, browser extension, or other piece of software to perform some of the methods and embodiments herein.

The designated user's client device 150 may be any device with a display configured to present information to a user of the device. In some embodiments, the client device presents information in the form of a user interface (UI) with multiple selectable UI elements or components. In some embodiments, the client device 150 is configured to send and receive signals and/or information to the processing engine 102 and/or hand hygiene device 140. In some embodiments, the client device is a computing devices capable of hosting and executing one or more applications or other programs capable of sending and/or receiving information. In some embodiments, the client device may be a computer desktop or laptop, mobile phone, virtual assistant, virtual reality or augmented reality device, wearable, or any other suitable device capable of sending and receiving information. In some embodiments, the processing engine 102 may be hosted in whole or in part as an application or web service executed on the client device 150. In some embodiments, one or more of the hand hygiene device 140, processing engine 102, and client device 150 may be the same device. In some embodiments, the designated user's client device 150 is associated with a designated user account within a hand hygiene platform. The designated user's client device 150 will be described in further detail below.

In some embodiments, optional repositories can include one or more of a use repository 130, compliance data repository 132, and/or settings repository 134. The optional repositories function to store and/or maintain, respectively, user information or user profiles associated with the hand hygiene device 140, compliance data captured from users of the hand hygiene device, and settings of the hand hygiene device, processing engine, and/or client device. The optional database(s) may also store and/or maintain any other suitable information for the processing or hand hygiene device 140 to perform elements of the methods and systems herein. In some embodiments, the optional database(s) can be queried by one or more components of system 100 (e.g., by the processing engine 102), and specific stored data in the database(s) can be retrieved.

Hand hygiene device 140 is a platform configured to facilitate video communication between two or more parties, such as within a conversation, video conference or meeting, message board or forum, virtual meeting, or other form of digital communication. The video communication session may be one-to-many (e.g., a speaker presenting to multiple attendees), one-to-one (e.g., two friends speaking with one another), or many-to-many (e.g., multiple participants speaking with each other in a group video setting).

FIG. 2 is a diagram illustrating an exemplary computer system 150 with software modules that may execute some of the functionality described herein.

II. Exemplary Methods

FIG. 2 is a flow chart illustrating an exemplary method that may be performed in some embodiments.

At step 210, the system detects, via a number of sensors, that a user is in proximity to a hand hygiene device. The user may be, e.g., a nurse or doctor within a hospital building where the hand hygiene device is located. In some embodiments, the system detects that the user is in proximity to a hand hygiene device via ultrasonic sensors, while in other embodiments motion sensors may be used, or any other sensing technology. The step functions to determine when someone approaches the device. In some embodiments, the sensors may be visible as holes on the side of the unit. In various embodiments, "in proximity" is determined to be within a certain predefined range, within the capabilities of the sensors to accurately detect a user approaching, or some other metric.

At step 212, the system provides instructions for the device to open a door to a compartment within the device. Upon the unit senses the user approaching as in step 210, the system instructs the device to open a door for a compartment which is designed to fit a mobile device. The compartment may have one door or two doors (i.e., one on each side of the device, where the compartment is the full width of the device). The device opens the door automatically upon the user being sensed as approaching. In some embodiments, the screen and/or speakers built-in or attached to the device may provide some instruction or notification to the user, such as, for example, "Please insert your mobile device into the compartment for disinfection."

At step 214, the system detects that a mobile device has been placed within the compartment. Upon the door opening in step 212, a user may place a mobile device into the compartment. In some embodiments, there is a tray, holder, or slot designed to fit a mobile device such as a smartphone. In other embodiments, the user simply places the device within the compartment. In some embodiments, the system detects that the device is in the compartment based on optical sensors, motion sensors, ultrasonic sensors, or any other sensing technology. In some embodiments, the system also will sense that a user's hands have been removed from the compartment.

At step 216, the system closes the door of the compartment. Now that the user has placed the mobile device within the compartment and removed his hands from the compartment, the system automatically closes the door of the compartment.

At step 218, the system performs disinfection of the mobile device within the compartment. In some embodiments, the system disinfects the mobile device via UV-C light irradiation, which is electrooptical in nature. In some embodiments, the disinfection may be performed by LED lights, mercury lamps, xenon lamps, exciter lamps, fluorescent lamps, or some other UV-C light source. The disinfection is performed through the dedicated compartment of the hand hygiene device, with any doors to the compartment closed firmly to avoid exposure of UV-C light irradiation to the user positioned near the device. In some embodiments, the amount of UV-C light is a dose previously programmed into the unit, without needing any input from the unit. The disinfection is performed in a completely automated, and touch-free way.

At step 220, concurrently to disinfecting the mobile device, the system detects that at least one hand of the user has been placed under a dispensing component of the hand hygiene device, and then instructs the dispensing component to dispense hand sanitizer. In some embodiments, upon the disinfection of step 218 being initiated on the mobile device, the screen and/or speakers of the hand hygiene device may provide some indication or notice to the user that the disinfection is underway, and that the user should insert his or her hands into the dispensing compartment to receive hand sanitizer. In some embodiments, the dispensing compartment may include LED lights to call the attention of the user. In some embodiments, the compartment is plastic, with internal LEDs. The dispensing compartment is a compartment large enough for a user's hands to be placed inside. In some embodiments, the compartment contains a sensor configured to sense when a hand is inside the compartment. In some embodiments, the sensor is optical in nature, while in others it may be a motion sensor, ultrasonic sensor, or any other sensing technology. In some embodiments, the sensor detects when a user's hand or hands are specifically underneath a dispensing component which is configured to dispense hand sanitizer.

Upon sensing the user's hand or hands inside of the dispensing compartment, positioned underneath a dispensing component, the system instructs the dispensing component to dispense hand sanitizer. In some embodiments, the dispensing component includes a peristaltic pump which is configured to dispense hand sanitizer. In some embodiments, the hand sanitizer is a liquid alcohol solution, while in others it may be a creamy solution or an alcoholic gel. In some embodiments, a simple cartridge or other container may be used to house the hand sanitizer inside of the hand hygiene device to be dispensed with the dispensing compartment. In some embodiments, rather than a proprietary cartridge which only works with the hand hygiene device but not other devices, the system can incorporate an open system, wherein any (or nearly any) bottle, container, or cartridge from any company can be adapted to work within the hand hygiene device. In some embodiments, an adapter is incorporated to adapt the bottle, container, or cartridge for use with the hand hygiene device. In this way, third parties may manufacture containers which will fit inside of the hand hygiene device, making the device flexible for a wide variety of containers and sanitizers.

In some embodiments, a preconfigured amount of hand sanitizer is dispensed by default. In some embodiments, the amount of sanitizer to be dispensed can be modified by the user or a designated user. A designated user is any user of the hand hygiene device who receives permission or possesses administrative authority to alter the functioning of the hand hygiene device in some way. Such permission may be granted via an administrative settings feature of the device, via an application which remotely connects to the device (such as via a wireless internet connection), or some other method.

For example, a hand hygiene device within a hospital may dispense 3 ml of alcohol by default. A dedicated user in the form of a hospital administrator may wish to change the settings of the device so that it dispenses 5 ml of alcohol rather than 3 ml. The administrator opens an application on her smartphone, which connects to the hand hygiene device remotely and shows a user interface (UI) to the administrator. The UI displays features and settings of the hand hygiene device. One setting allows the administrator to alter the amount of sanitizer to be dispensed and/or the amount of alcohol within the sanitizer to be dispensed. The administrator changes this setting, closes the app, and the device's setting is altered accordingly.

In some embodiments, the dispensing component itself may be adjusted automatically in order to allow for an adjustment to the output of the dispensing component. For example, if a designated user changes the output from 3 ml to 5 ml of alcohol, a new dispensing nozzle may be necessary. The device may respond by automatically switching the nozzle from a 3 ml output nozzle to a 5 ml output nozzle. In some embodiments, the dispensing component includes one or more such interchangeable dispensing nozzles and is configured to allow for adjustment of the output of the dispensing component.

At step 222, upon completion of the disinfection of the mobile device, the system opens the door to the compartment to release the mobile device to the user. In some embodiments, the disinfection of the mobile device will complete on its own without any input needed from the user. Upon the disinfection completing, the system instructs the device to automatically open the compartment doors. The user is then free to retrieve the mobile device from the compartment. If the user has finished sanitizing his hands in the meantime, the user is then free to continue on his or her way, having complied with hand hygiene during this session by completing all steps of sanitizing hands and disinfecting the mobile device.

In some embodiments, the screen and the one or more speakers of the hand hygiene device may display audiovisual content during the disinfection of the mobile device, the dispensing of the hand sanitizer, or both. This audiovisual content may be, e.g., advertising or marketing content, instructional content (for example, instructions on how to wash hands properly), informational content (for example, facts or statistics about mobile devices harboring bacteria or the importance of hand hygiene in preventing the spread of infectious diseases), or any other suitable audiovisual content. In some embodiments, the device is configured to display one or more pieces of data relating to hand hygiene compliance with respect to the usage of the device generally or usage of the device by the specific user in question. In some embodiments, the device may display a checklist for satisfying hand hygiene compliance, including checked or unchecked boxes indicating whether the user has satisfied a given item on the checklist or not.

In some embodiments, the audiovisual content displayed provides positive reinforcement to the user and/or nearby users to encourage hand hygiene compliance. For example, if a user completes hand sanitization and mobile device disinfection on the device, the device may provide some audiovisual reinforcement congratulating the user on successful compliance, which nearby users may see and/or hear. In this sense, an aspect of social positive reinforcement may be incorporated by congratulating users while they are nearby colleagues, thus encouraging those colleagues to comply as well. Many other forms and examples of positive reinforcement may be considered. Some examples of audiovisual positive reinforcement may include, e.g., emojis, video of someone saying thanks, clapping, or a bell sound.

In some embodiments, the system receives one or more requests from a client device to remotely modify the audiovisual content. The client device may be associated with a designated user, such as an administrator with permission to modify the device. As described above, the designated user may sign into an application on the user's mobile device or computer which connects to the hand hygiene device and allows the user to modify settings of the device and otherwise configure the device. The device then modifies the audiovisual content in response to the one or more requests. The designated user may, for example, switch the audiovisual content from advertising or marketing material to information material, display certain pieces of positive reinforcement to encourage hand hygiene compliance, or display other material.

In some embodiments, the hand hygiene device can be configured remotely via a dedicated control application or "app". Such a control application may be present on a designated user's client device, e.g. a computer or smartphone. In some embodiments, the designated user can use this control application to access compliance data remotely via the control application, modify one or more settings remotely, or otherwise access and control the device from a remote location.

Within some embodiments, the hand hygiene device collects usage data associated with the mobile device disinfection and hand sanitizer dispensation, and then transmits the usage data to a remote server and/or cloud storage. This data may be transmitted and stored for later viewing by one or more designated users, thus providing useful data on compliance and usage to administrators and other individuals. In some embodiments, designated users may remotely access the usage data, such as via an application on a client device associated with the designated user (e.g., a mobile device or computer). In some embodiments, upon release of the mobile device to the user during step 222, the system sends, to at least one client device associated with a designated user, notification of the user checking in or clocking in at a designated area associated with the hand hygiene device. This provides the ability for users to "check in" or "clock in" to a particular area or location. For example, an employee of a company may sanitize his hands and disinfect his mobile device before entering the office building where he works. Upon completion of the process at the hand hygiene device, the system sends notification to his supervisor that he has clocked into work. The notification may be an email, push notification to a mobile device, text, an automatic addition of an entry to a time entry logging software, or any other suitable notification, alert, or change to a particular application or piece of software.

FIG. 3 is a flow chart illustrating an optional exemplary method that may be performed in some embodiments concurrently to or after the steps of FIG. 2.

At optional step 310, the system provides, via a screen and one or more speakers on the hand hygiene device, audiovisual content during the disinfection of the mobile device, the dispensing of the hand sanitizer, or both. As described above, in various embodiments the audiovisual content may be advertising or marketing content, informational or instructive content, usage or compliance data, or any other suitable content. In some embodiments, third party advertisements may be displayed via an advertising arrangement with the owners or administrators of the hand hygiene device.

At optional step 312, the system receives one or more requests from a client device to remotely modify the audiovisual content. As described above, a designated user may remotely connect to the hand hygiene device via an application on a computer or smartphone, and request to change one or more settings for displaying audiovisual content.

At optional step 314, the system modifies the provided audiovisual content in response to the one or more requests. Upon receiving the request to change the audiovisual content, the system modifies the display to a different piece of content.

III. Exemplary Embodiments

FIGS. 4A-4H are diagrams illustrating various aspects of the systems and methods herein through different example embodiments of a hand hygiene device.

Figure 4A:
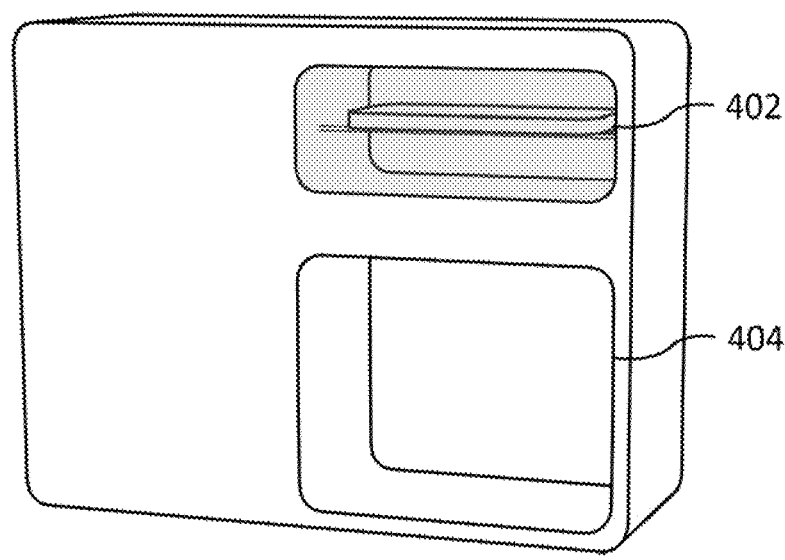
FIG. 4A is a diagram illustrating one example embodiment of a hand hygiene device, according to some embodiments.

FIG. 4A is a diagram illustrating one example embodiment of a hand hygiene device, according to some embodiments. The hand hygiene device includes a mobile device compartment 402 and a dispensing compartment 404. The functionality and characteristics of both compartments have been described above. The hand hygiene device appears in a box-like form, but in other embodiments the hand hygiene device may take any suitable form. The compartments may also be in any suitable size, shape, or form. The mobile device compartment 402 is illustrated with a mobile device inserted, resting on a holder within the compartment. In some embodiments, one or more doors to the compartment may be present, and are configured to open and close automatically based on sensing of mobile device and hands within the compartment or lack thereof.

Figure 4B:
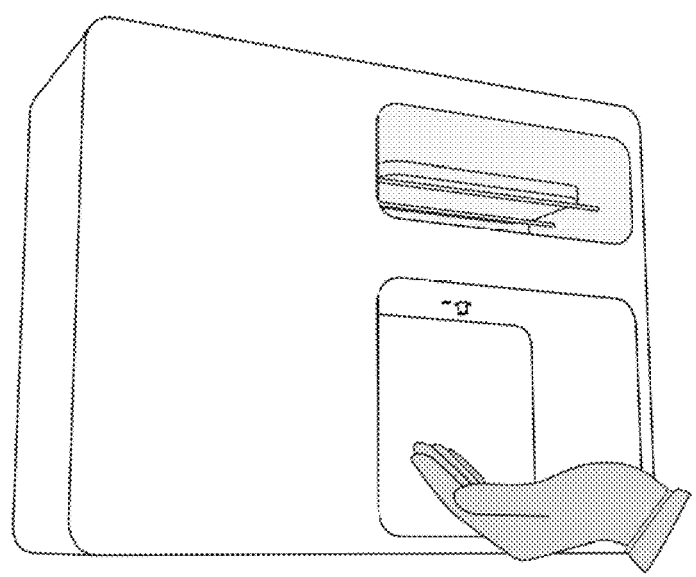
FIG. 4B is a diagram illustrating one example embodiment of a hand hygiene device with a user placing hands within a dispensing component, according to some embodiments.

FIG. 4B is a diagram illustrating one example embodiment of a hand hygiene device with a user placing hands within a dispensing component, according to some embodiments. In this illustration, the hand hygiene device from FIG. 4A is depicted with a user inserting his hands into the dispensing compartment. A sensor placed in the compartment senses the user's hands, and hand sanitizer is dispensed into the user's hands automatically without the user needing to touch any component.

Figure 4C:
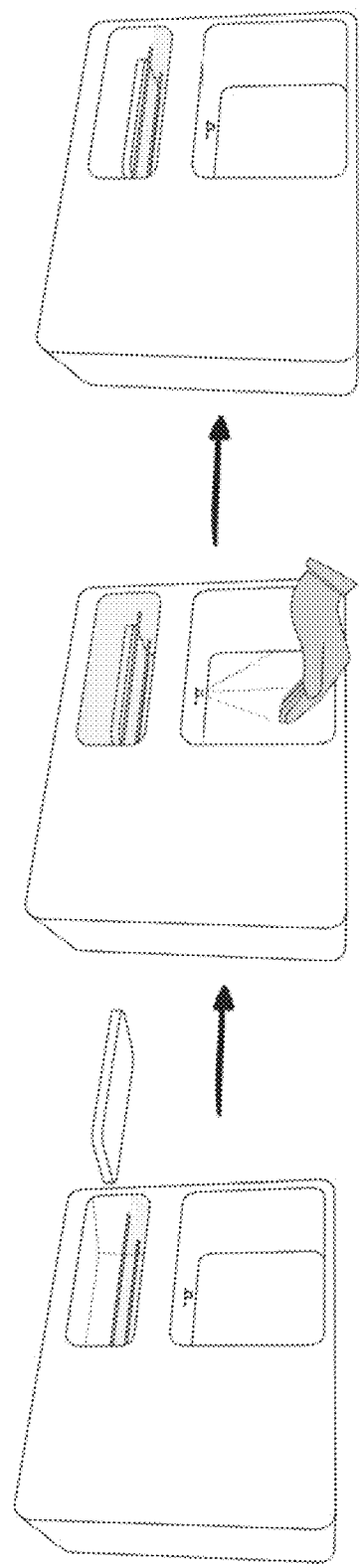
FIG. 4C is a diagram illustrating one example embodiment of a hand hygiene device in operation, according to some embodiments.

FIG. 4C is a diagram illustrating one example embodiment of a hand hygiene device in operation, according to some embodiments. In the first image, a user places a mobile device into the mobile device compartment. The compartment senses the device and automatically closes the door. The compartment then starts UV-C irradiation to disinfect the mobile device.

In the second image, while the disinfection is underway, the user concurrently places a hand into the dispensing compartment. A sensor at the top of the dispensing compartment senses the presence of the hand inserted, and automatically dispenses the hand sanitizing solution.

In the third image, once the configured dose of UV-C is irradiated, the door automatically opens for the user to retrieve the device. From beginning to end, the depicted process may take as little as 25-30 seconds. Such a timeframe may be so minimal in part because of the speed typically associated with UV-C disinfection, i.e., approximately 20-30 seconds, as well as the recommended time for a user to properly sanitize hands, i.e., approximately 20-30 seconds.

Figure 4D:
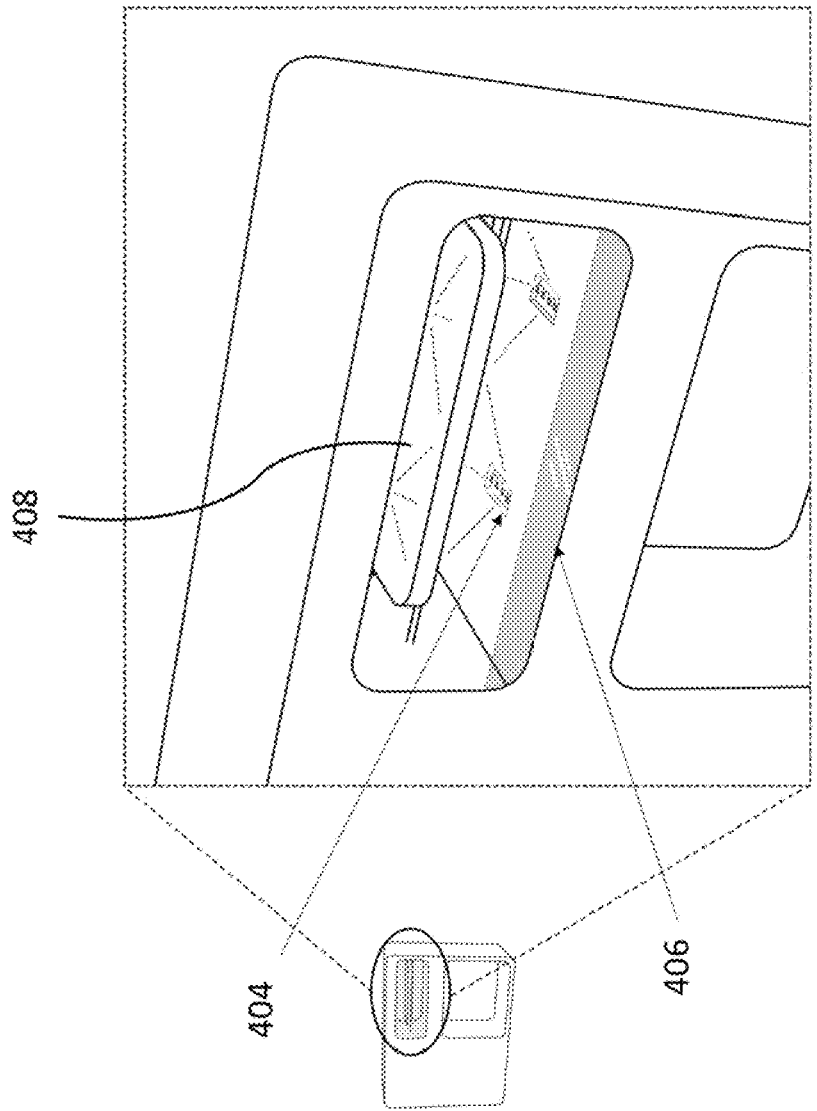
FIG. 4D is a diagram illustrating one example embodiment of a mobile device compartment in operation, according to some embodiments.

FIG. 4D is a diagram illustrating one example embodiment of a mobile device compartment in operation, according to some embodiments. The mobile device compartment depicted includes at least one UV-C irradiation light source 404, an automatic door 406 to stop UV-C exposure to the user, and a mobile device 408 inserted into a tray, or holder of the mobile device compartment. Upon the door automatically closing, the UV-C light sources are activated to disinfect the mobile device. The door then automatically opens upon completion of the disinfection.

Figure 4E:
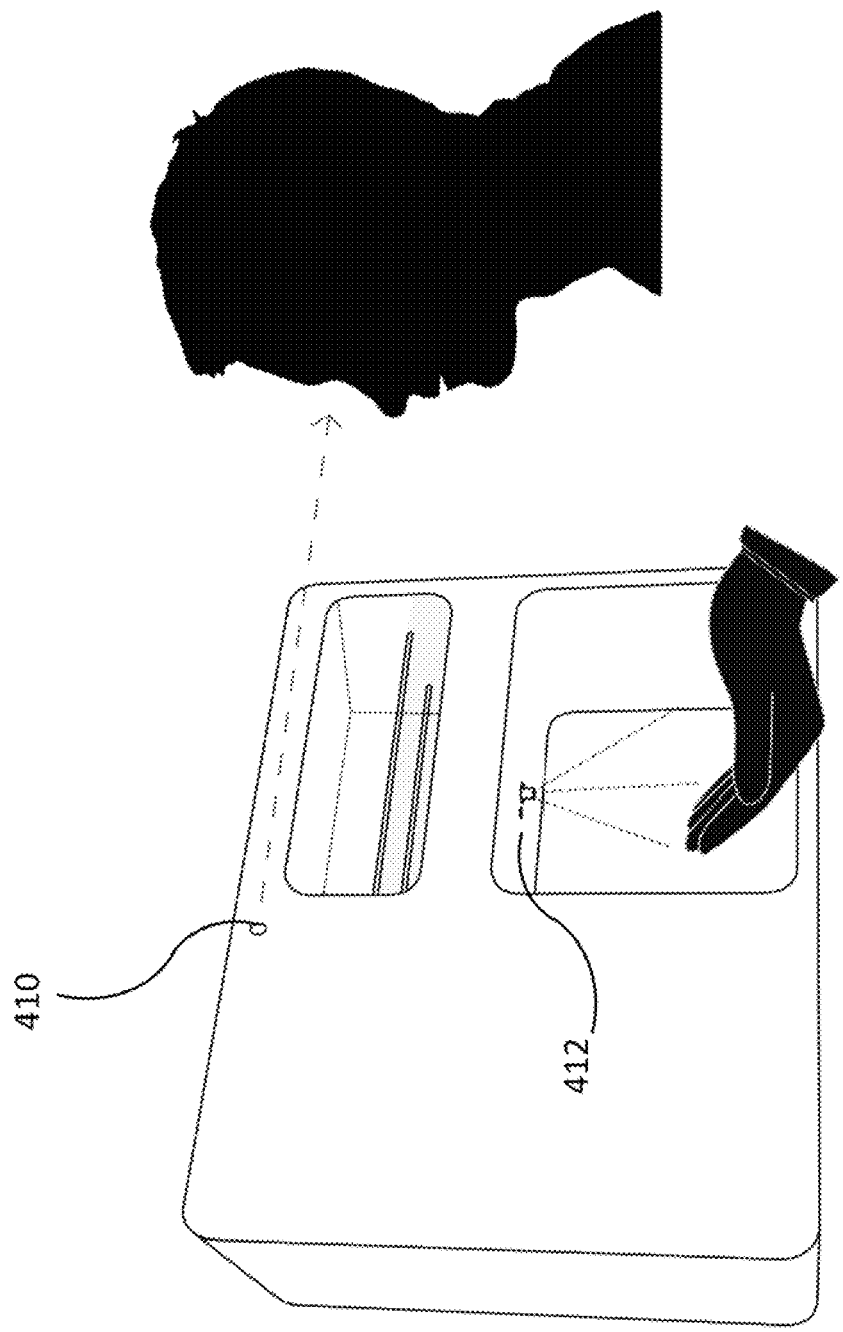
FIG. 4E is a diagram illustrating one example embodiment of sensors within a hand hygiene device, according to some embodiments.

FIG. 4E is a diagram illustrating one example embodiment of sensors within a hand hygiene device, according to some embodiments. As depicted in the illustration, the unit senses a user approaching via a sensor 410, which may be an ultrasonic sensor or any other sensing technology. Upon the unit sensing the user approaching, the unit opens the automatic door of the mobile device compartment. A user may then place a mobile device inside for disinfection. A unit may also contain a sensor 412 placed within the dispensing compartment, which senses a user's hand or hands being inserted into the compartment. Upon sensing the user's hand(s), the unit dispenses the hand sanitizer solution.

Figure 4F:
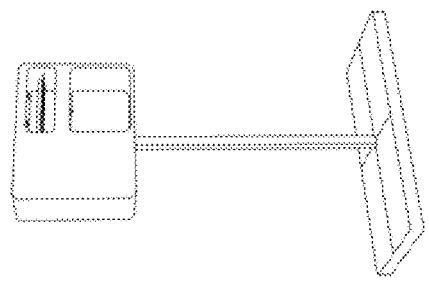
FIG. 4F is a diagram illustrating one example embodiment of hand hygiene devices in a wall-mounted and a free-standing configuration, according to some embodiments.
Figure 4F:
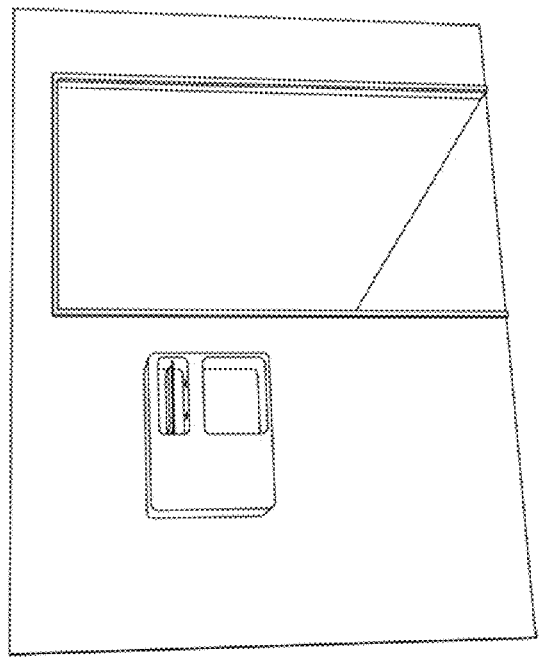

FIG. 4F is a diagram illustrating one example embodiment of hand hygiene devices in a wall-mounted and a free-standing configuration, according to some embodiments. As shown on the left image, the hand hygiene device may be wall-mounted within an environment, thus reducing the space taken up by the device in a heavily trafficked area. As shown on the right image, the hand hygiene device may instead by free-standing within an environment by being mounted on a stand. This may be beneficial in environments where a wall is not near to the ideal placement of the device, or where extra attention is desired for the presence of the device in the environment.

Figure 4G:
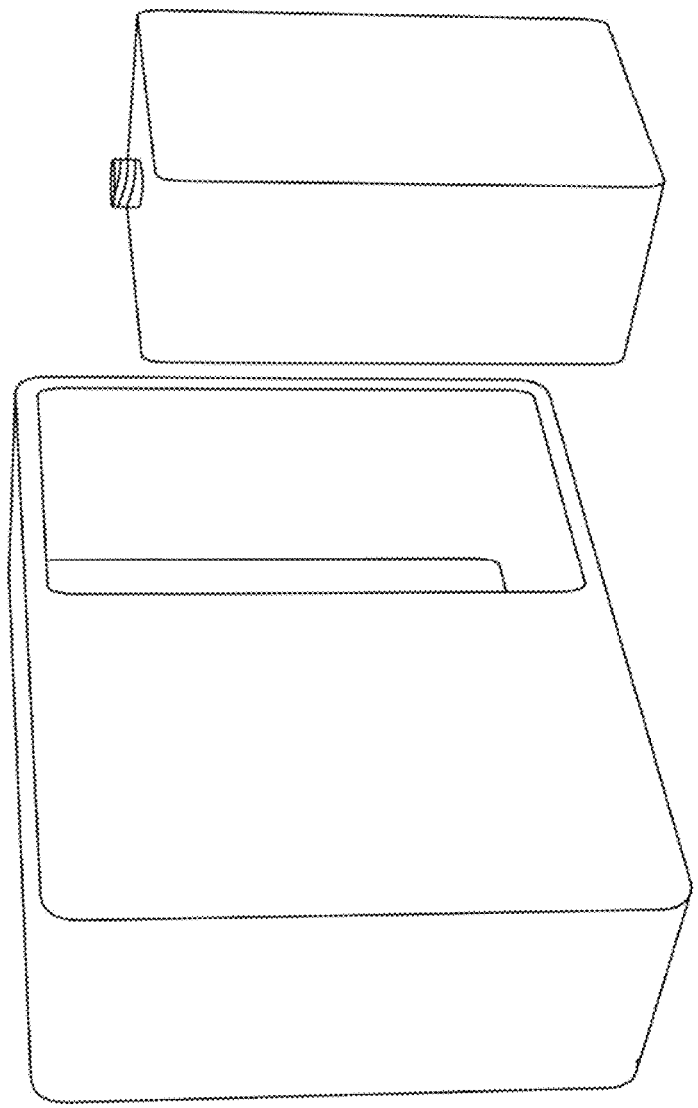
FIG. 4G is a diagram illustrating one example embodiment of a hand sanitizer container being placed within a dispensing component, according to some embodiments.

FIG. 4G is a diagram illustrating one example embodiment of a hand sanitizer container being placed within a dispensing component, according to some embodiments. The illustration depicts a hand hygiene device with its own container for filling or refilling hand sanitizer to be dispensed. The container fits inside the dispensing component and provides a solution for the dispensing component to be filled with hand sanitizer. The container can then be removed upon completion of the filling.

Figure 4H:
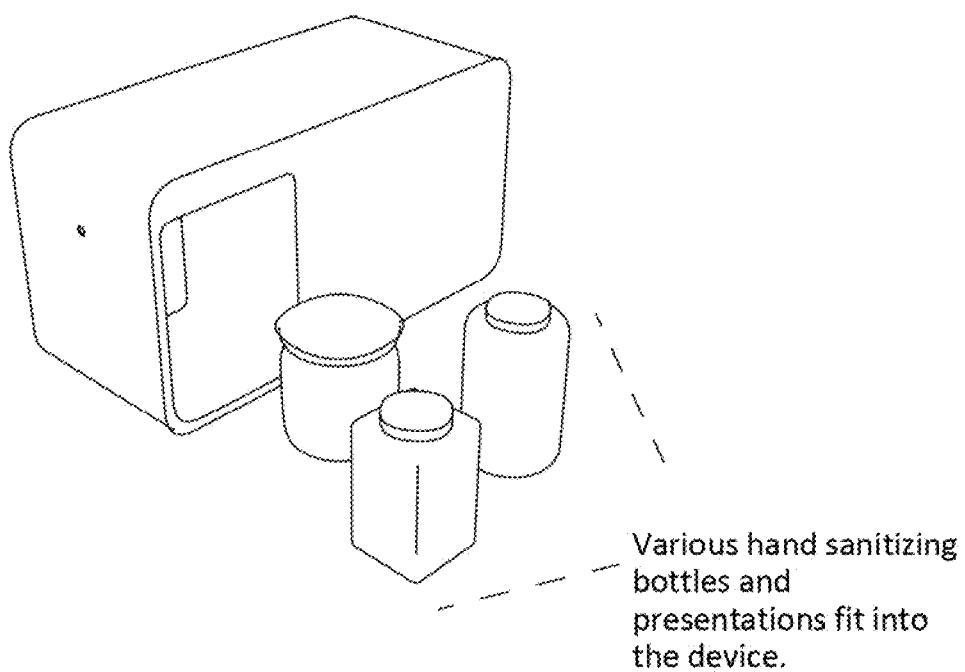
FIG. 4H is a diagram illustrating one example embodiment of differently shaped containers being placed within a dispensing component, according to some embodiments.

FIG. 4H is a diagram illustrating one example embodiment of differently shaped containers being placed within a dispensing component, according to some embodiments. In some embodiments, the device is able to fit different bottles, containers, or cartridges of hand sanitizing and cleaning solutions, as described above. This may include different caps, dimensions, shapes, and presentations of containers.

Providing Hand Hygiene Compliance Data at an Intelligent Hand Hygiene Device

Some embodiments of the present invention may include systems and methods for providing hand hygiene compliance data at an intelligent hand hygiene device. Such embodiments may provide more complex and sophisticated features around collecting compliance data, associating the data with a user, determining one or more compliance rates of individual users, groups of users, the device, or a designated area, and transmitting the compliance rate to a client device associated with a designated user, such as an administrator of the hand hygiene device.

In one embodiment, the system detects, via a plurality of sensors, that a user is in proximity to the hand hygiene device. The system then matches the user to one or more user profiles within the system. The system detects that at least one hand of the user has been placed under a dispensing component of the hand hygiene device, then instructs the dispensing component to dispense hand sanitizer without the user coming into physical contact with the hand hygiene device. The system then proceeds to collect compliance data for the user corresponding to hand hygiene compliance, and associates the compliance data for the user with the one or more user profiles corresponding to the user. The system then determines or updates a compliance rate of the user based at least on the compliance data associated with the user. The system finally transmits the compliance rate of the user to at least one client device associated with at least one designated user.

In some embodiments, the system may use facial recognition technology to detect the face of a user and match the face of the user to one or more existing user profiles within the system.

In some embodiments, the system generates aggregate compliance data based on at least the compliance data, and then assigns the aggregate compliance rate to one or more of: a group of users, a hand hygiene device, and/or a designated area.

IV. Exemplary Methods for Providing Hand Hygiene Compliance Data

FIG. 5 is a flow chart illustrating an exemplary method that may be performed in some embodiments.

At step 510, the system detects, via a number of sensors, that a user is in proximity to a hand hygiene device. In some embodiments, this step may be similar or identical to step 210 of FIG. 2. In some embodiments, the system may use facial recognition technology to detect the face of a user. The hand hygiene device may include a built-in camera or other sensor to facilitate the facial recognition. Such a camera or sensor is aimed at the face of the user, and may be adjusted to account for different heights of users. In some embodiments, upon capturing a photograph or image data of a user, the captured facial data is then compared to one or more images of facial data associated with users of the hand hygiene device, via user accounts or profiles within the system. This facial recognition technology can be used for recognizing regular or repeat users, such as nurses or doctors who check in and out of a designated area every day or multiple times a day.

At step 512, the system matches the user to one or more user profiles within the system. In some embodiments, this may be performed with facial recognition technology, and may consist of matching captured facial data to existing facial data for user profiles or accounts, as described above. In some embodiments, an RFID or similar sensor may be placed in the form of a badge, tag, or other form of identification in order to identify users. Any other suitable form of identification may be contemplated.

At step 514, the system detects that at least one hand of a user has been placed under a dispensing component of the hand hygiene device. This step is similar or identical to step 220 of FIG. 2, albeit with or without the concurrent disinfection of a mobile device being performed.

At step 516, the system instructs the dispensing component to dispense hand sanitizer without the user coming into physical contact with the device. This step is similar or identical to step 220 of FIG. 2, albeit with or without the concurrent disinfection of a mobile device being performed.

At step 518, the system collects compliance data for the user corresponding to hand hygiene compliance. In some embodiments, compliance data includes data on whether individual users have complied by sanitizing their hands or performing other hand hygiene processes using the device. It may contain a list of times the user has complied, along with time stamps for each instance. It may additionally or alternately contain a list of times the user has passed by the device without complying, i.e., without performing hand sanitization processes on the device. Compliance data may or may not be associated with an individual.

In some embodiments, the system generates aggregate compliance data based on at least the compliance data, then assigns the aggregate compliance data to one or more of a group of users, a hand hygiene device, and/or a designated area. Aggregate compliance data is compliance data that has been aggregated (i.e., summed or combined) across multiple users. Aggregation may include combining the compliance data of all users for a specific hand hygiene device in question; combining the compliance data of a specific group of users, e.g., all nurses within the hospital; or combining the compliance data of a designated area, e.g., all users within the maternity ward of a hospital. In some embodiments, any combination of different users, groups, areas, or devices may be used to aggregate compliance data.

In some embodiments, the system further provides, via the screen and/or the one or more speakers of the hand hygiene device, at least a subset of the aggregate compliance data, along with audio and/or visual notification regarding at least one of a group of users, a hand hygiene device, or a designated area with respect to compliance with a predefined hand hygiene standard. For example, upon generating aggregate compliance data for all nurses within the hospital, this compliance data may be displayed on the screen of the device, thus alerting all nurses and others within the hospital on the compliance or non-compliance of nurses with respect to hand hygiene. This may provide a positive reinforcement to improve hand hygiene compliance.

In some embodiments, the system provides, to at least one client device associated with at least one designated user, the aggregate compliance data in real time or substantially real time upon the aggregate compliance data being assigned. A designated user, such as a hospital administrator, may thus be able to retrieve a given set of aggregate compliance data for a given group, device, or area of the hospital. This retrieval may be done via an application of a mobile device or computer which remotely connects to the hand hygiene device.

In some embodiments, a "snapshot" may be provided within a user interface to one or more designated users at one or more client devices. The snapshot may consist of various pieces of aggregate compliance data for one or more groups of users, one or more hand hygiene devices, and/or one or more designated areas. The snapshot may act as a dashboard of information within the user interface, providing designated users with a quick overview of a number of hand hygiene devices at once along with data about groups, areas, and more. Compliance data and/or compliance rates may be displayed. In some embodiments, preventive or corrective actions may be displayed to be taken for one or more groups of users, hand hygiene devices, and/or designated areas which are falling below a minimum compliance rate for those particular groups of users, hand hygiene devices, and/or designated areas.

In some embodiments, this snapshot is displayed or updated in real time or substantially real time upon compliance data being collected by hand hygiene devices. For example, the system may display the snapshot to be refreshed or updated every few seconds, every minute, or every five minutes.

In some embodiments, a notification may be sent to one or more designated users at a client device informing the user that a particular hand hygiene device, group of users, or designated area has fallen below the designated minimum compliance rate for that device, group, or area. The notification may allow the designated user to take some action, such as preventive or corrective action, upon being informed of the failure to meet minimum compliance rate. For example, a user may get a notification that Hand Hygiene Device #7 has fallen below the minimum compliance rate, and may present the user with a suggested corrective action to display a warning or caution message on the screen of the device.

At step 520, the system associates the compliance data for the user with the one or more user profiles corresponding to the user. The system, which previously matched the detected user with a user profile within the system, can thus associate the captured compliance data with that specific user profile.

At step 522, the system determines or updates a compliance rate of the user based at least on the compliance data associated with the user. The compliance rate is a rate by which the user has complied with hand hygiene standards by utilizing the device, compared to the overall times the user has passed by in proximity to the device. Thus, a rate of 80% compliance may be determined for a particular doctor who has passed by the device 10 times, and has used the device to sanitize his hands 8 out of the 10 times.

At step 524, the system transmits the compliance rate of the user to at least one client device associated with at least one designated user. The designated user may be, for example, an administrator of a hospital, or any other user granted permission or authority to receive sets of compliance rates from the device. The compliance rates may be transmitted via a client device (e.g., a mobile device or computer) associated with the designated user, wherein an application of the mobile device can remotely connect to the hand hygiene device.

In some embodiments, the system provides, via the screen and/or the one or more speakers, at least a subset of the compliance data of the user along with audio and/or visual notification regarding at least whether the user is in compliance with a predefined hand hygiene standard. Thus, audiovisual content displayed on the screen and/or played on the speakers may provide a notice of the user's compliance data, including potentially the user's compliance rate. The content may display information that, for example, a user has complied with hand hygiene standards this time, has complied at a certain rate this month, or has complied at a certain rate overall.

In some embodiments, the system determines or updates a compliance rate of the user based at least on the compliance data associated with the user, and then transmits the compliance rate of the user to at least one client device associated with at least one designated user, as described above.

In some embodiments, the system displays one or more preventive or corrective actions to be performed by the hand hygiene device in response to the compliance rate of one or more users, a hand hygiene device, or a designated area failing to comply with a predefined hand hygiene standard. A preventive or corrective action may be, for example, displaying or presenting an audio notification that low hand hygiene compliance has been detected for the user, for the hand hygiene device as a whole, for the designated area, or for some other grouping. In some embodiments, a door may not open or unlock unless hand hygiene processes have been complied with. In some embodiments, a notification may be automatically sent to a user's supervisor within the organization, a hospital administrator, or to some other designated user upon the user's compliance rate being too low. Many other possibilities for corrective or preventive actions may be contemplated.

In some embodiments, the system receives, via a client device associated with at least one designated user, a request to insert, modify, or delete at least one of the one or more preventive or corrective actions to be performed by the hand hygiene device, then modifies the preventive or corrective actions accordingly based on the request. This may be performed remotely via an application on the client device, as described above.

In some embodiments, the system is configured to detect an opportunity, wherein an opportunity relates to a user being in proximity to the hand hygiene device. The opportunity is detected when there is an opportunity for a user to make use of the hand hygiene device or to pass by the device without engaging the device. In some embodiments, the system is further configured to detect an event, wherein the user in proximity to the device decides to engage with the device during the opportunity, such that the user proceeds with one or more hand hygiene processes at the device. In some embodiments, the compliance rate for a user is determined based on one or more detected opportunities and one or more detected events for the user. For example, one formula for determining the compliance rate for the user may be from the formula: Compliance Rate=(Events/Opportunities)×100. Other such formulas may be contemplated in various embodiments.

In some embodiments, the system determining a current compliance rate for the hand hygiene device, compares the current compliance rate with the minimum compliance rate for the device, and if the current compliance rate does not meet the threshold of the minimum compliance rate, providing an audio and/or visual notification of lack of hand hygiene compliance via at least one of the hand hygiene device and/or at least one client device associated with at least one designated user. This allows for notification to be provided when current compliance rates of the device do not meet a minimum standard. Positive reinforcement and/or corrective actions may be provided accordingly.

In some embodiments, one or more presets within the device may be selected by a designated user remotely via a client device. Presents may relate to particular conditions which may require heightened or lessened requirements for compliance. For example, a preset may be set during outbreak conditions, wherein setting the preset includes increasing the min compliance rate for one or more hand hygiene devices, and displaying more aggressive or flashing visuals on the screen, as well as a strong audio alarm on the speakers. Many different variations of presets can be contemplated.

In some of the embodiments, designated users can set some of hand hygiene devices to have the minimum compliance rate that the user wants. Such settings may be facilitated via an application on the client device of the designated user. For example, a user may opt to change the settings of a hand hygiene device to accept only 100% compliance rate as a minimum, i.e., all users must comply with hand hygiene standards or the device fails the minimum compliance rate.

In some embodiments, one or more functions of the hand hygiene device are configured to be controllable remotely from at least one client device associated with at least one designated user, as described above.

In some embodiments, the system may additionally capture, via one or more sensors, biometric data for the user. This may include any suitable biometric data relating to health, hygiene, or sanitization. The system then transmits the biometric data to at least one client device associated with at least one designated user. This may be useful for such examples as determining that a doctor or nurse is sick and transmitting that data to an administrator who may be able to proceed with next steps to prevent or mitigate the spread of sickness within the environment.

Figure 6A:
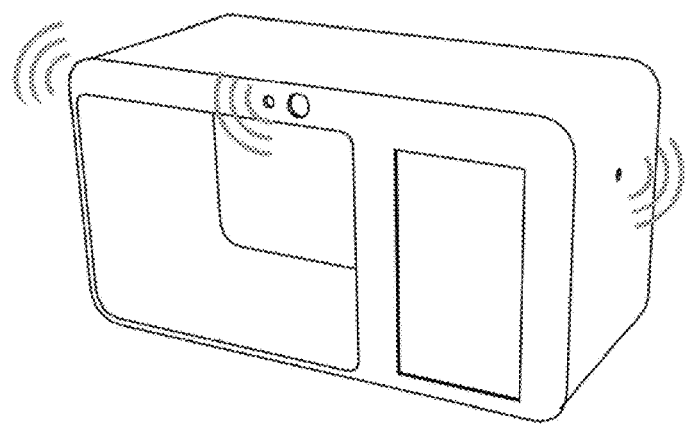
FIG. 6A is a diagram illustrating one example embodiment of sensors within a hand hygiene device, according to some embodiments.

FIG. 6A is a diagram illustrating one example embodiment of sensors within a hand hygiene device, according to some embodiments. Built-in sensors may include infrared, ultrasonic, laser, or any other sensing technology, as described above.

Figure 6B:
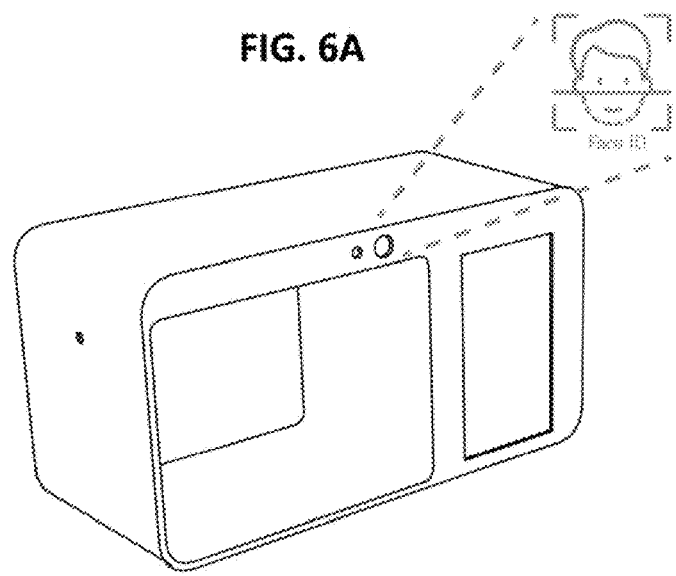
FIG. 6B is a diagram illustrating one example embodiment of facial recognition technology being utilized within a hand hygiene device, according to some embodiments.

FIG. 6B is a diagram illustrating one example embodiment of facial recognition technology being utilized within a hand hygiene device, according to some embodiments. A built-in camera within the device performs facial recognition on a user in order to identify and match that user with a user profile within the system. In some embodiments, the system then can assign the user their own hand hygiene compliance rate, without the need for any user to wear an RFID sensor or tag or similar identification sensors.

Figure 6C:
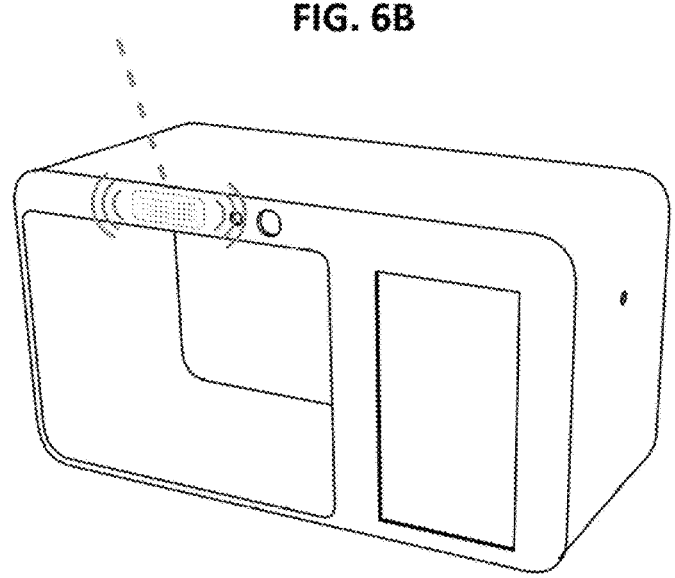
FIG. 6C is a diagram illustrating one example embodiment of RFID-based identification being utilized within a hand hygiene device, according to some embodiments.

FIG. 6C is a diagram illustrating one example embodiment of RFID-based identification being utilized within a hand hygiene device, according to some embodiments. In some embodiments, RFID-based identification may be employed. The RFID technology picks up data on RFID-based badges, tags, or other forms of identification worn or carried on the persons of users. This data helps to identify the user and match him with a user profile within the system. This may be used in place of facial recognition technology or other technology for identification.

Figure 7A:
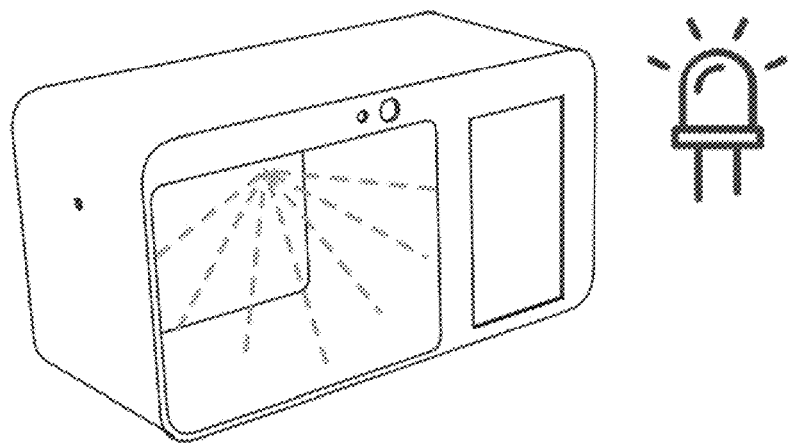
FIG. 7A is a diagram illustrating one example embodiment of LED lighting being utilized within a hand hygiene device, according to some embodiments.

FIG. 7A is a diagram illustrating one example embodiment of LED lighting being utilized within a hand hygiene device, according to some embodiments. LED lighting may appear within the dispensing compartment of the device in order to alert the user to the functionality of hand sanitizer which can be dispensed into the user's hands. In various embodiments, this LED lighting may be configured to be activated upon the user inserting a mobile device into a mobile device compartment, or may be present by default when no user is utilizing the device.

Figure 7B:
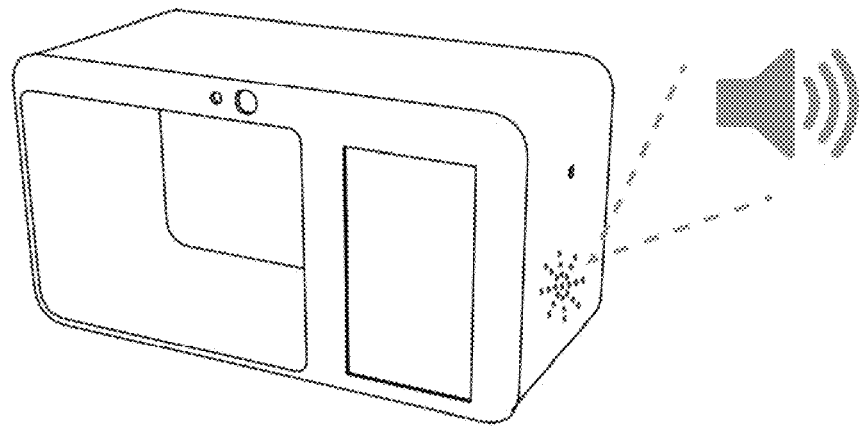
FIG. 7B is a diagram illustrating one example embodiment of speakers being utilized within a hand hygiene device, according to some embodiments.

FIG. 7B is a diagram illustrating one example embodiment of speakers being utilized within a hand hygiene device, according to some embodiments. In this illustration, built-in speakers are present on one side of the device. The built-in speakers are capable of emitting audio, such as voice-based notification of compliance data, compliance rates, upcoming events, advertisements, or more.

Figure 7C:
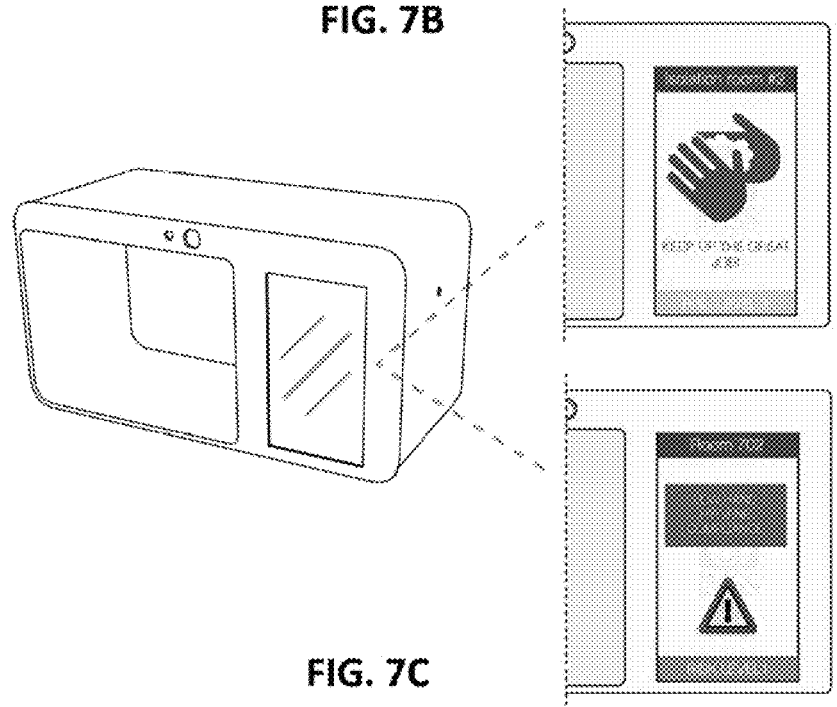
FIG. 7C is a diagram illustrating one example embodiment of a screen being utilized within a hand hygiene device, according to some embodiments.

FIG. 7C is a diagram illustrating one example embodiment of a screen being utilized within a hand hygiene device, according to some embodiments. In various embodiments, the screen may be configured to displayed positive reinforcement to improve hand hygiene compliance, as in the top image reading "keep up the great job!", reinforcement when compliance levels are low, as in the bottom image reading "low hand hygiene compliance", or any other audiovisual content.

Figure 8:
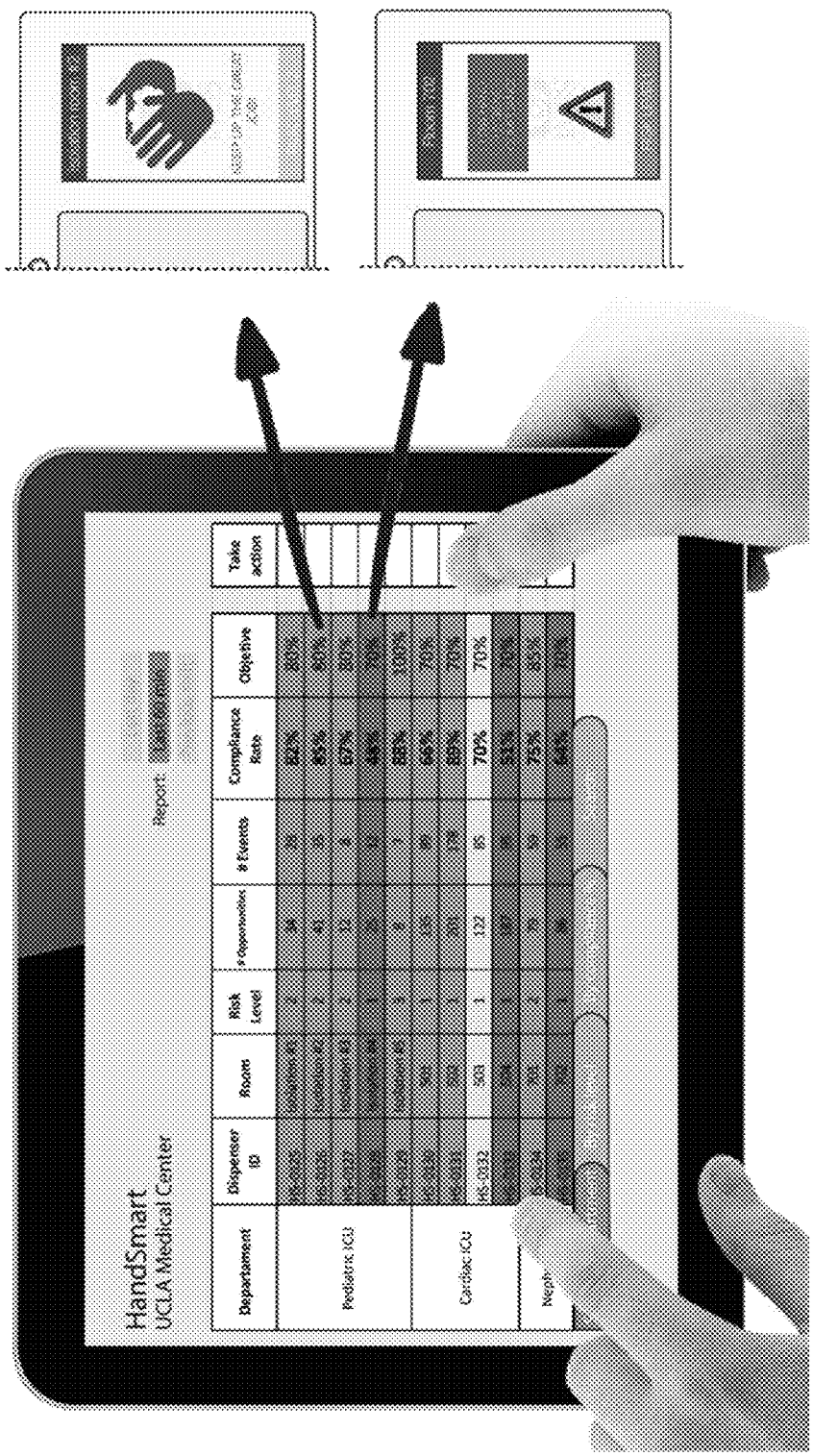
FIG. 8 is a diagram illustrating one example embodiment of a compliance data being remotely accessed by a designated user, according to some embodiments.

FIG. 8 is a diagram illustrating one example embodiment of a compliance data being remotely accessed by a designated user, according to some embodiments. Within the illustration, a designated user uses an application on the user's tablet device to remotely connect to the hand hygiene device via a wireless internet connection. The designated user is then able to view a user interface depicting relevant compliance data. This particular compliance data is labeled for the UCLA Medical Center in particular, and includes information on risk levels, opportunities and events, compliance rates, objectives, and corrective or preventive actions to be taken (if any). This data is separated out into individual designated areas such as the Pediatric ICU and Cardiac ICU; individual hand hygiene devices (Dispenser ID); and individual rooms (e.g., Isolation #1 and Isolation #2). If a low compliance rate is discovered for a particular area or hand hygiene device, corrective action may be requested by the designated user via the application, and the hand hygiene device will be modified to institute the corrective action. In this example, a hand hygiene device with a good compliance rate will receive positive reinforcement in the form of an encouraging audiovisual display (the top depicted screen), while a hand hygiene device with a poor compliance rate will receive a warning notification (the bottom depicted screen).

Figure 9:
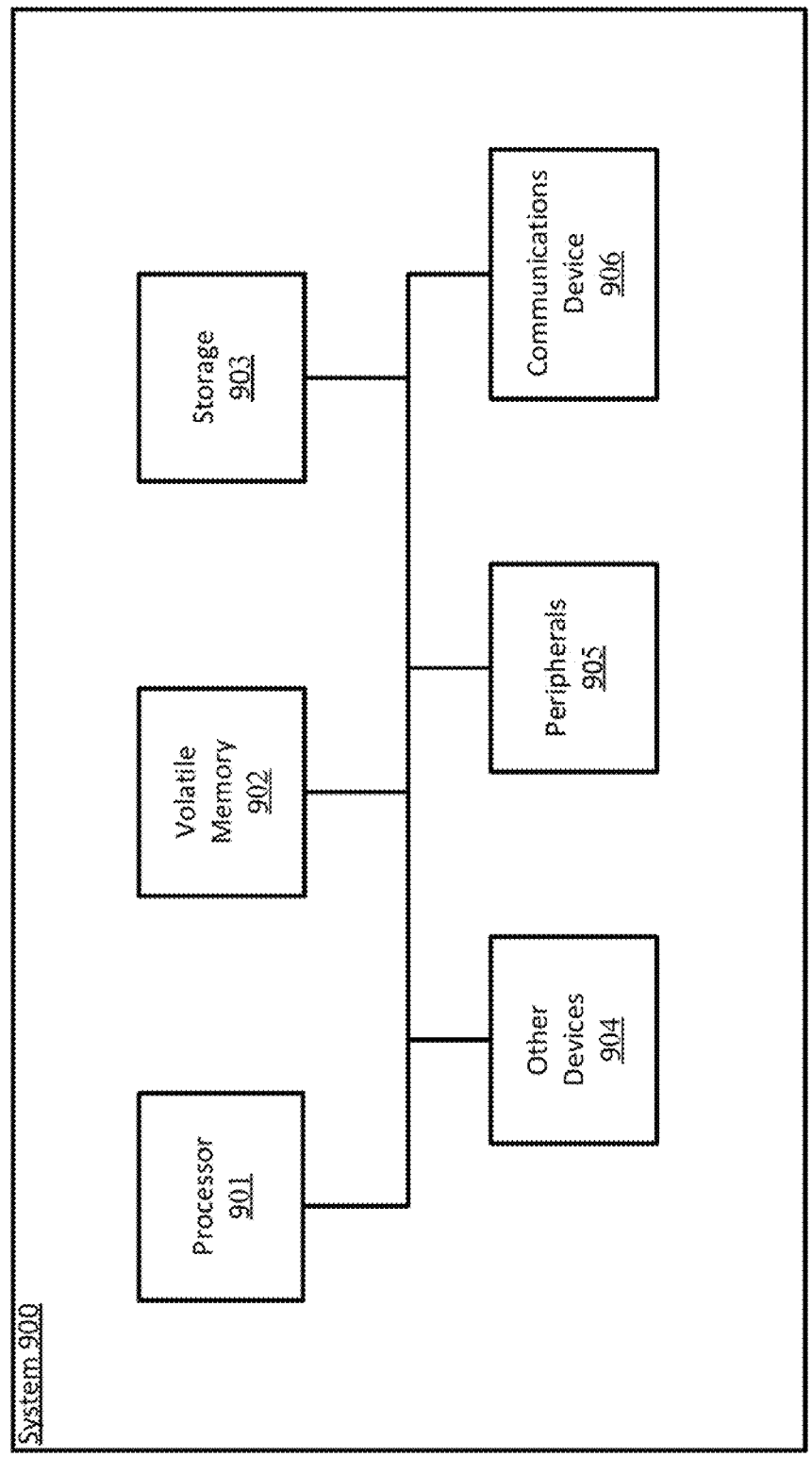
FIG. 9 is a diagram illustrating an exemplary computer that may perform processing in some embodiments.

FIG. 9 is a diagram illustrating an exemplary computer that may perform processing in some embodiments. Exemplary computer 900 may perform operations consistent with some embodiments. The architecture of computer 900 is exemplary. Computers can be implemented in a variety of other ways. A wide variety of computers can be used in accordance with the embodiments herein.

Processor 901 may perform computing functions such as running computer programs. The volatile memory 902 may provide temporary storage of data for the processor 901. RAM is one kind of volatile memory. Volatile memory typically requires power to maintain its stored information. Storage 903 provides computer storage for data, instructions, and/or arbitrary information. Non-volatile memory, which can preserve data even when not powered and including disks and flash memory, is an example of storage. Storage 903 may be organized as a file system, database, or in other ways. Data, instructions, and information may be loaded from storage 903 into volatile memory 902 for processing by the processor 901.

The computer 900 may include peripherals 905. Peripherals 905 may include input peripherals such as a keyboard, mouse, trackball, video camera, microphone, and other input devices. Peripherals 905 may also include output devices such as a display. Peripherals 905 may include removable media devices such as CD-R and DVD-R recorders/players. Communications device 906 may connect the computer 100 to an external medium. For example, communications device 906 may take the form of a network adapter that provides communications to a network. A computer 900 may also include a variety of other devices 904. The various components of the computer 900 may be connected by a connection medium such as a bus, crossbar, or network.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "determining" or "executing" or "performing" or "collecting" or "creating" or "sending" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

Various general purpose systems may be used with programs in accordance with the teachings herein, or it may prove convenient to construct a more specialized apparatus to perform the method. The structure for a variety of these systems will appear as set forth in the description above. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (e.g., a computer). For example, a machine-readable (e.g., computer-readable) medium includes a machine (e.g., a computer) readable storage medium such as a read only memory ("ROM"), random access memory ("RAM"), magnetic disk storage media, optical storage media, flash memory devices, etc.

In the foregoing disclosure, implementations of the disclosure have been described with reference to specific example implementations thereof. It will be evident that various modifications may be made thereto without departing from the broader spirit and scope of implementations of the disclosure as set forth in the following claims. The disclosure and drawings are, accordingly, to be regarded in an illustrative sense rather than a restrictive sense.

What is claimed is:

1. A method for providing hand hygiene and mobile device disinfection at a hand hygiene device, comprising:
    detecting, via a plurality of sensors, that a user is in proximity to the hand hygiene device;
    in response to detecting that a user is in proximity, providing instructions for the device to open a door to a compartment within the device;
    detecting that a mobile device has been placed within the compartment;
    in response to detecting that the mobile device has been placed within the compartment, closing the door to the compartment;
    performing disinfection of the mobile device within the compartment;
    concurrently to performing disinfection of the mobile device:
        detecting that at least one hand of the user has been placed under a dispensing component of the hand hygiene device,
        instructing the dispensing component to dispense hand sanitizer without the user coming into physical contact with the hand hygiene device, and
        providing, to at least a screen and one or more speakers connected to or embedded in the hand hygiene device, audiovisual content directed to the user, wherein the audiovisual content is manually modifiable by one or more designated users via one or more remote devices associated with the one or more designated users, and wherein the one or more remote devices are remotely connected to the hand hygiene device via a network; and
    upon completion of the disinfecting of the mobile device, opening the door to the compartment to release the mobile device to the user.

2. The method of claim 1, wherein manually modifying the audiovisual content comprises:
    receiving, from one of the remote devices associated with one of the designated users, a request to remotely modify the audiovisual content, the request comprising one or more manual modifications to the audiovisual content; and
    modifying the audiovisual content in response to the request.

3. The method of claim 1, wherein the audiovisual content comprises positive reinforcement messages encouraging users to improve hand hygiene compliance.

4. The method of claim 1, further comprising:
    receiving, via a client device connected to the hand hygiene device via a control application, a request to modify one or more settings of the hand hygiene device; and
    in response to receiving the request, remotely modifying one or more settings of the hand hygiene device.

5. The method of claim 1, wherein the disinfection of the mobile phone is performed by optical radiation of UV-C light.

6. The method of claim 1, further comprising:
    collecting usage data associated with the mobile device disinfection and hand sanitizer dispensation; and
    transmitting the usage data to a remote server and/or cloud storage.

7. The method of claim 6, further comprising:
    providing, via a control application on a client device, remote access of the usage data to the client device.

8. The method of claim 1, further comprising:
    receiving configuration instructions for the hand hygiene device from a client device associated with a designated user; and
    configuring the hand hygiene device according to the configuration instructions.

9. The method of claim 8, wherein the configuration instructions comprise at least configuration of the amount of hand sanitizer to be dispensed.

10. The method of claim 1, wherein the dispensing component comprises a pumping mechanism which allows for the dispensing of hand sanitizer, and wherein the hand sanitizer is one of a liquid, gel, or cream sanitizing or cleaning solution.

11. The method of claim 1, wherein the dispensing component comprises one or more interchangeable dispensing nozzles configured to allow for adjustment of the output of the dispensing component.

12. The method of claim 11, wherein the output of the dispensing component is adjusted according to a request or instruction received from a client device associated with a designated user.

13. The method of claim 1, further comprising:
    upon release of the mobile device to the user, sending, to at least one client device associated with a designated user, notification of the user checking in or clocking in at a designated area associated with the hand hygiene device.

14. The method of claim 1, further comprising:
upon detecting that the mobile device has been placed within the compartment, detecting one or more pieces of identifying information from the mobile device; and
sending the one or more pieces of identifying information to at least one client device associated with a designated user.

15. A system for providing hand hygiene and mobile device disinfection at a hand hygiene device, the system comprising one or more processors configured to perform the operations of:
detecting, via a plurality of sensors, that a user is in proximity to the hand hygiene device;
in response to detecting that a user is in proximity, providing instructions for the device to open a door to a compartment within the device;
detecting that a mobile device has been placed within the compartment;
in response to detecting that the mobile device has been placed within the compartment, closing the door to the compartment;
performing disinfection of the mobile device within the compartment;
concurrently to performing disinfection of the mobile device:
detecting that at least one hand of the user has been placed under a dispensing component of the hand hygiene device,
instructing the dispensing component to dispense hand sanitizer without the user coming into physical contact with the hand hygiene device, and
providing, to at least a screen and one or more speakers connected to or embedded in the hand hygiene device, audiovisual content directed to the user, wherein the audiovisual content is manually modifiable by one or more designated users via one or more remote devices associated with the one or more designated users, and wherein the one or more remote devices are remotely connected to the hand hygiene device via a network; and
upon completion of the disinfecting of the mobile device, opening the door to the compartment to release the mobile device to the user.

16. The system of claim 15, wherein the audiovisual content comprises positive reinforcement messages encouraging users to improve hand hygiene and mobile device disinfection compliance.

17. The system of claim 15, further comprising:
receiving, via a client device connected to the hand hygiene device via a control application, a request to modify one or more settings of the hand hygiene device; and
in response to receiving the request, remotely modifying one or more settings of the hand hygiene device.

18. The system of claim 15, wherein the disinfection of the mobile phone is performed by optical radiation of UV-C light.

* * * * *